(12) United States Patent
Colburn et al.

(10) Patent No.: US 6,699,842 B1
(45) Date of Patent: Mar. 2, 2004

(54) DOMINANT NEGATIVE DELETION MUTANTS OF C-JUN AND THEIR USE IN THE PREVENTION AND TREATMENT OF CANCER

(75) Inventors: Nancy H. Colburn, Middletown, MD (US); Zigang Dong, Frederick, MD (US); Powel H. Brown, North Potomac, MD (US); Michael J. Birrer, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1,537 days.

(21) Appl. No.: 08/213,433

(22) Filed: Mar. 10, 1994

(51) Int. Cl.$^7$ .......................... A01N 43/04; A61K 31/70
(52) U.S. Cl. ......................................... 514/44; 424/93.2
(58) Field of Search ............................... 424/93.1, 93.2; 514/44; 536/23.1

(56) References Cited

PUBLICATIONS

Blau et al (1995) New Eng. J. Med., 1204–1207.*
Mulligan (1993) Science 260, 926–932.*
Science News Report (1995) Science 269, 1050–1055.*
Anderson (1994) Hu. Gene Ther. 5, 281–282.*
Russell (1994) Eu. J. Cancer 30 A, 1165–1171.*
Gutierrez et al (1992) The Lancet 339, 715–721.*
Grimm et al (1994) Current Op. Oncol. 6, 96–105.*
Bernstein, L.R. et al. "AP1/jun Function is Differentially Induced In Promotion–Sensitive and Resistant JB6 Cells" *Science*, 244:566–569 (1989).
Brown, P.H. et al. "Machanism of Action of a Dominant–Negative Deletion Mutant of c–Jun" *Oncogene*, 9:791–799 (1994).
Pfarr, C.H., et al. "Mouse JunD Negatively Regulates Fibroblast Growth and Antagonizes Transformation By ras" *Cell*, 76:747–760 (1994).
Monteclaro, F.S., et al. "A Jun–binding Protein Related to a Putative Tumor Suppressor" *Proc. Nat'l. Acad. Sci.*, 90:6726–6730 (1993).
Auwerx, J., et al. "IP–1: A Dominant Inhibitor of Fos/Jun Whose Activity is Modulated By Phosphorylation" (1992) *Cell*, 64:983–993 (1991).
Domann, F.E., et al. "Stable Expression of a c–Jun Deletion Mutant In Two Malignant Mouse Epidermal Cell Lines Blocks Tumor Formation In Nude Mice" *Cell Growth Diff.*, 5:9–16 (1994).
Hirai, et al. "Both Jun and Fox Contribute to Transcription Activation By the Heterodimer" *Oncogene*, 5:39–46 (1990).
Baichwall, et al. "Control of c–Jun Activity by Interaction of a Cell–Specific Inhibitor with Regulatory Domain: Differences Between v–and c–Jun" *Cell*, 63:815–525.
Abate, et al. "Transcriptional Regulation by Fos and Jun in Vitro: Interaction Among Multiple Activator and Regulatory Domains" *Mol. Cell. Biol.*, 11:3624–3632 (1991).
Alani, et al. The Transactivating Domain of the c–Jun Proto–Oncoprotein is Required for Cotransformation of Rat Embryo Cells *Mol. Cell. Biol.*, 11–6286–6295.
Ben–Ari, et al. "Differential c–Jun Expression in Response to Tumor Promoters in JB6 Cells Sensitive or Resistant to Neoplastic Transformation" *Mol. Carcinogenesis*, 5:62–74 (1992).
Brown, et al. "Suppression of Oncogene–Induced Tranformation By a Deletion Mutant of C–Jun" *Oncogene*, 8:877–886 (1993).
Dong, et al. "Blocking of Tumor Promoter–Induced AP–1 Activity Inhibits Induced Transformation in JB6 Mouse Epidermal Cells" *Proc. Natl. Acad. Sci. USA*, 91:609–613.

* cited by examiner

*Primary Examiner*—Deborah Crouch
(74) *Attorney, Agent, or Firm*—Venable, LLP

(57) ABSTRACT

The inhibition of AP-1 activity by dominant negative deletion mutants of c-jun is disclosed. This inhibition of AP-1 activity is shown to be associated with inhibition of tumor promoter-induced neoplastic transformation. Therefore, the invention relates to the utilization of dominant negative deletion mutants of c-jun which are inhibitory to tumor promotor-induced neoplastic transformation as therapeutic agents in the prevention and treatment of cancer in mammals.

12 Claims, 10 Drawing Sheets

```
                        SEQUENCE LISTING (1) GENERAL INFORMATION:

(iii) NUMBER OF SEQUENCES:  3

(2) INFORMATION FOR SEQ ID NO:1:

(i) SEQUENCE CHARACTERISTICS:
        (A) LENGTH:  18 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION: SEQ ID NO:1:

GCAAGAAGCA TTTCTTGG                                                    18

(2) INFORMATION FOR SEQ ID NO:2:

(i) SEQUENCE CHARACTERISTICS:
        (A) LENGTH:  19 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION: SEQ ID NO:2:

CAGGAGCGGA TCAAGGCAG                                                   19

(2) INFORMATION FOR SEQ ID NO:3:

(i) SEQUENCE CHARACTERISTICS:
        (A) LENGTH:  18 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION: SEQ ID NO:3:

ACAGGACCCT GAGTGGTT                                                    18
```

DOMINANT NEGATIVE DELETION MUTANTS OF C-JUN AND THEIR USE IN THE PREVENTION AND TREATMENT OF CANCER

FIELD OF INVENTION

The present invention is in the field of tumor biology. More specifically, the present invention relates to use in vivo of dominant negative deletion mutants of c-jun in methods for the treatment and prevention of cancer.

BACKGROUND OF INVENTION

Chemical carcinogenesis is a multistep process that includes initiation, promotion and progression (Boutwell, R. K. (1964) *Prog. Exp. Tumor Res.,* 4: 207–250; Drinkwater, N. R. (1989) In: *Genes and Signal Transduction in Multistage Carcinogenesis,* (ed) Colburn, N. H., Marcel Dekker, Inc., New York, pp. 3–17); Dong, Z. et al. (1990) *Cancer Invest.,* 8: 523–533; Weinstein, I. B. (1988) *Cancer Res.,* 48: 4135–4143) with the rate-limiting steps in multistage carcinogenesis occurring during the promotion and progression phases. Numerous studies have shown that tumor promotion is a long term process that is partially reversible and that requires chronic exposure to tumor promoter. In vivo studies in the mouse have also found susceptibility to promotion of neoplastic transformation to be inheritable and genetically controlled (Drinkwater, N. R. (1989)).

In recent years, numerous cellular oncogenes have been implicated in the transactivation of genes implicated in cellular growth and differentiation. One such cellular oncogene, c-jun, encodes a 39-kDa nuclear phosphoprotein c-jun which is a component of the heterodimeric transcriptional activator AP-1 along with the c-Fos proto-oncoprotein. (Karin, M. et al. (1991) *Biochem. Biophys. Acta.,* 1072: 129–157; Vogt, P. K. et al (1990) *Adv. Cancer Res.,* 55: 1–35; Curran, T. et al. (1988) *Cell.,* 55: 395–397). The AP-1 complex has been demonstrated to transcriptionally activate genes that contain the sequence TGAg/cTCA, referred to as an AP-1 binding site or TPA-responsive element (TRE), in their promoters (Karin, M. and Angel, P. (1991) *Biochim. Biophys. Acta.,* 1072: 129–157, Vogt, P. K. et al (1990) *Adv. Cancer Res.,* 55: 1–35, Curran, T. et al (1988) *Cell.,* 55: 395–397). In addition to the induction of AP-1 activity by TPA treatment, AP-1 activity has also been shown to be blocked by retinoic acid (RA) and glucocorticoids (Schule, R. et al. (1990) *Cell,* 62: 1217–1226; Schule, R. et al. (1991) *Proc. Natl. Acad. Sci. USA.,* 88: 6092–6096; Nicholson, R. C. et al. (1990) *EMBO. J.,* 9: 4443–4454; Jonat, C. et al. (1990) *Cell,* 62: 1189–1204; Yang, N. et al. (1991) *Proc. Natl. Acad. Sci. USA.,* 88: 3559–3563). Of interest, several genes that may be involved in tumor promotion or progression have been shown to respond to AP-1 including the genes for the metalloproteinases collagenase and stromelysin (transin) (Matrisian, L. M. et al. (1991) *Am. J. Medic. Sci.,* 302: 157–162, Angel, P., et al. (1987) *Mol. Cell. Biol.,* 7: 2256–2266, Honoki, K. et al. (1992) *Mol. Carcinogenesis.,* 6: 122–128).

Analysis of the c-jun and c-fos phoshoproteins has demonstrated that they each contain basic DNA-binding domains, a leucine zipper domain involved in dimerization, and transactivation domains involved in transcriptional regulation (Alani et al. (1991) *Mol. Cell Biol.,* 11:6286–6295). The c-jun protein, through protein-protein interactions within the leucine zipper domain, is able to dimerize with itself (Smeal, T. et al. (1989) *Genes Dev.,* 3: 2091–2100; Turner, R. et al. (1989) *Science,* 243: 1689–1694) or with other leucine zipper-containing proteins such as other c-jun family members (JunB or JunD) (Halazonetis T. D. et al. (1988) *Cell,* 55: (917–924), fos family members (c-Fos, FosB, Fra-1 or Fra-2) (Smeal, T. et al. (1989); Turner, R. et al. (1989); and Zerial, M. et al. (1989) *Embo J.,* 8: 805–813), the cyclic AMP-responsive element binding protein (CREB) (Sassone-Corsi, P. et al. (1990) *Oncogene,* 5: 427–431) and potentially other yet unidentified leucine zipper proteins.

Recent studies of the c-jun proto-oncogene have revealed that the regions critical for transcriptional activation include the dimerization domain, the DNA-binding domain, and an area within the amino terminal half of the c-jun protein that functions as a transcriptional activation domain (Hirai, S. et al. (1990) *Oncogene,* 5: 39–46; Baichwal, V. R. et al. (1990) *Cell,* 63: 815–825; and Abate, C. et al. (1991) *Mol. Cell. Biol.,* 11: 3624–3632. Studies by Alani et al. (1991) *Mol. Cell. Biol.,* 11: 6286–6295) demonstrated that regions of c-jun required for transcriptional activation are the same as those required for c-jun/ras-induced transformation of rat embryo cells thereby suggesting that c-jun might transform cells by altering gene expression through dysregulated DNA transcription. More recently, Brown et al. ((1993) *Oncogene,* 8: 877–886)) have shown that a dominant negative c-jun mutant which specifically blocked AP-1 activity also blocked H-ras plus c-jun induced cellular co-transformation. In addition, extensive evidence showing that endogenous hormones and growth factors play a major role in tumor promotion in human carcinogenesis suggests that tumor promoter-induced transformation is an important step in how humans actually get cancer. Thus, identification of dominant negative deletion mutants of c-jun which are capable of suppressing tumor promoter-induced neoplastic transformation might be of great utility in the prevention of carcinogenesis in vivo.

SUMMARY OF INVENTION

The present invention relates to a method of preventing carcinogenesis in mammals comprising: administering to a mammal at least one deletion mutant of c-jun inhibitory to tumor promoter-induced neoplastic transformation in an amount effective to prevent carcinogenesis.

The invention also provides pharmaceutical compositions for the prevention of carcinogenesis in mammals where said pharmaceutical compositions comprise at least one deletion mutant of c-jun inhibitory to tumor promoter-induced neoplastic transformation in a suitable diluent or carrier.

The invention further relates to a method for treating cancer comprising: administering to a mammal having cancer at least one deletion mutant of c-jun inhibitory to tumor promoter-induced neoplastic transformation in a therapeutically effective amount.

The deletion mutants of the present invention may be a protein or a nucleic acid sequence encoding the protein. It is therefore an object of the present invention to provide nucleic acid sequences capable of directing production of deletion mutants of c-jun in a host organism. Such nucleic acid sequences may be obtained by PCR amplification of cloned c-jun DNA or by restriction digestion and linker ligation of cloned c-jun DNA in a plasmid. For purposes of this application, nucleic acid sequence refers to RNA, DNA, cDNA or any synthetic variant thereof which encodes a deletion mutant of c-jun protein.

It is also an object of the present invention to provide deletion mutants of c-jun where said deletion mutants are proteins inhibitory to tumor promoter-induced neoplastic transformation.

The present invention also relates to a method for determining whether a tumor promoter induces transformation via a c-jun dependent pathway, said method comprising: (a) transfecting a cell line transformable by treatment with said tumor promoter with nucleic acid sequence encoding a deletion mutant of c-jun inhibitory to tumor promoter-induced neoplastic transformation; (b) treating transfected and untransfected cells with said tumor promoter in an amount effective to stimulate neoplastic transformation of said cells; and (c) measuring transformation of said transfected and untransfected cells by a suitable transformation assay.

DESCRIPTION OF FIGURES

In FIG. 2A, the transfected cells were treated with either 0.1% DMSO, 10 ng/ml TPA, $10^{-7}$ M Fluocinolone acetonide(FA) in the absence of 10 ng/ml TPA (FA7), or $10^{-9}$, $10^{-8}$, and $10^{-7}$ M FA in the presence of 10 ng/ml TPA (TFA9, TFA8, and TFA7, respectively). In FIG. 2B, the transfected cells were treated with either 0.1% DMSO, 10 ng/ml TPA, $10^{-5}$ M retinoic acid (RA) in the absence of 10 ng/ml TPA (RA5) or at $10^{-7}$, $10^{-6}$, and $10^{-5}$ M RA in the presence of 10 ng/ml TPA (TRA7, TRA6, and TRA5) respectively. The results of the CAT assays are again expressed as the relative rate of accumulation of $^{14}$C-acetylated product.

In FIG. 3A, cells were exposed to either 3 ng/ml TPA alone, 0.01% DMSO alone, $10^{-9}$ M FA in the presence of 3 ng/ml TPA (TFA9), $10^{-8}$ M FA in the presence of 3 ng/ml TPA (TFA8), $10^{-7}$ M FA in the presence of 3 ng/ml TPA (TFA7) or to $10^{-8}$ M FA or $10^{-7}$ M FA alone. In FIG. 3B, cells were exposed to either 3 ng/ml TPA alone, 0.01% DMSO alone, $10^{-6}$ M retinoic acid alone, or $10^{-9}$ M-$10^{-6}$ M retinoic acid in the presence of 3 ng/ml TPA (TRA9, TRA8, TRA7, and TRA6 respectively). Cells were scored for colonies after 14 days in agar and transformation response in both FIGS. 3A and 3B was expressed as the number of soft-agar colonies/$10^4$ suspended cells.

FIG. 4 represents a composite of two different gels. The background of the vector control (N1) is darker than the gels from the TAM67 transfected cells (M4, M3 and M6) because it was exposed for a greater length of time.

In FIG. 5A, the DMSO treated groups have no error bars since they are control groups with values designated as basal level of CAT and normalized as one.

DETAILED DESCRIPTION OF INVENTION

Figure 1:
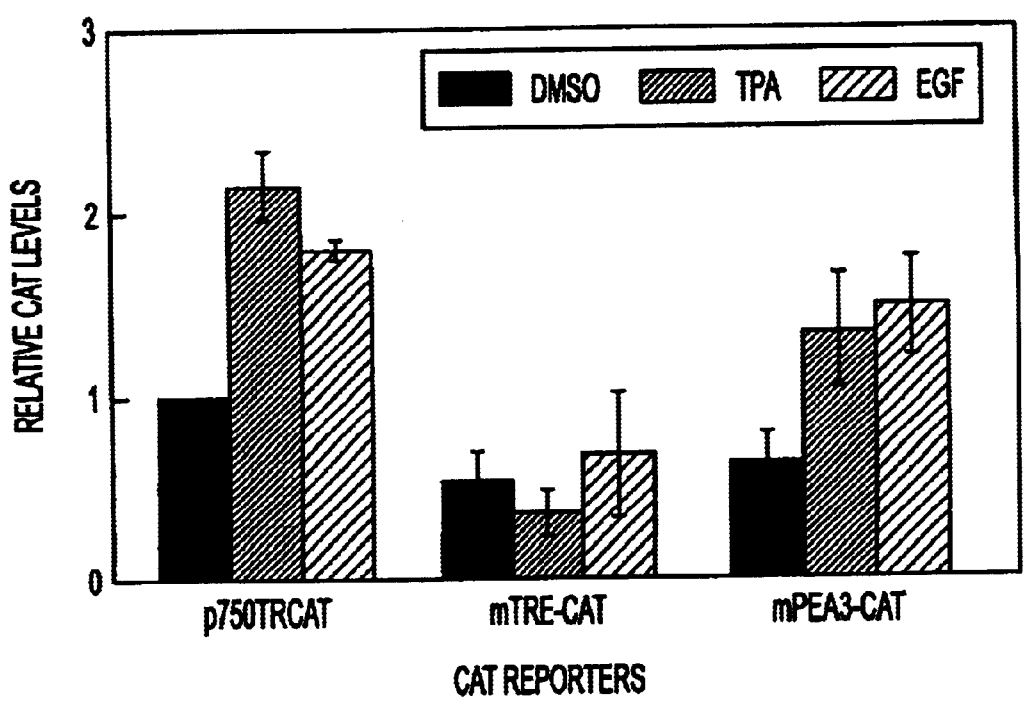
FIG. 1 shows the results of CAT assays in which aliquots of cell extracts prepared from transfected JB6 P+ $^{Cl}$ 41 cells were assayed for CAT activity following treatment for eight hours with either 0.1% dimethylsulfoxide (DMSO), 10 ng/ml of epidermal growth factor (EGF) or 10 ng/ml of 12-O-tetradecanoyl phorbol 13-acetate (TPA). Prior to the above treatment, cells were transfected with 10 µg of the CAT reporter plasmids P750TRCAT or mTRE-CAT or mPEA3-CAT and 10 µg sheared genomic DNA isolated from the CL 41 cells. The results are expressed as the rate of accumulation of $^{14}$C acetylated product relative to solvent controls and represent the mean±SEM of three experiments.

The present invention relates to dominant negative deletion mutants of c-jun inhibitory to tumor promoter-induced neoplastic transformation. More specifically, the present invention relates to methods of preventing and/or treating carcinogenesis in mammals via the use of dominant negative deletion mutants of c-jun as therapeutic agents.

In one embodiment, the present invention relates to a method of preventing carcinogenesis in mammals comprising: administering to a mammal at least one deletion mutant of c-jun inhibitory to tumor promoter-induced neoplastic transformation of preneoplastic cells in an amount effective to prevent carcinogenesis. "Deletion mutant of c-jun" is a dominant negative deletion mutant inhibitory to tumor promoter-induced neoplastic transformation of pre-neoplastic cells where the deletion refers to a deletion(s) made in the 39 kDa c-jun protein encoded by full-length c-jun DNA. The deletion mutant(s) of c-jun to be used in the above method may be a protein or it may be a nucleic acid sequence encoding the protein.

Variations are contemplated in the nucleic acid sequences of the present invention which will result in nucleic acid sequence that is capable of directing production of analogs of the deletion mutants of c-jun. Due to the degeneracy of the genetic code, it is to be understood that numerous choices of nucleotides may be made that will lead to a nucleic acid sequence capable of directing production of the instant deletion mutants or analogs thereof. As such, nucleic acid sequences which are functionally equivalent to sequences encoding the deletion mutants of the present invention are intended to be encompassed within the present invention. The functional equivalence of these sequences can be determined by one of ordinary skill in the art by testing such a nucleic acid sequence in the transactivation and transformation assays described in Examples 5 and 6 respectively of the present specification.

In one embodiment, the nucleic acid sequence used in the present method may be produced from full length c-jun DNA (Schütte, J. J. et al (1989) *Proc. Natl. Acad. Sci. USA*, 86: 2257–2261) by techniques of deletion mutagenesis known to one skilled in the art (Sambrook, J. et al. (1989) in "Molecular Cloning, A Laboratory Manual," Cold Spring Harbor Laboratory Press, Cold Spring Harbor, N.Y.)). Such deletion techniques include, but are not limited to, PCR amplification of a portion of cloned full-length c-jun DNA (Alani et al. (1991)) or restriction digestion and linker ligation of cloned c-jun DNA. In an alternative embodiment, the nucleic acid sequences of the present invention may be synthesized by an automated oligonucleotide synthesizer or may be custom ordered and prepared.

The deletions of the present invention are of sufficient size to produce a deletion mutant inhibitory to tumor promoter-induced neoplastic transformation of pre-neoplastic cells.

The preferred sizes of the deletions of the present invention range from about 80 amino acids to about 300 amino acids. In one embodiment, the deletion removes the entire transactivation domain of c-jun leaving the DNA-binding and leucine zipper domain intact. In an alternative embodiment, the deletion removes the entire transactivation and DNA-binding domains leaving only the leucine zipper domain intact. In yet another embodiment, the entire transactivation domain and part of the DNA-binding domain are removed. Deletions of the present invention include, but are not limited to, a deletion from amino acids 3 to 122 of c-jun; a deletion from amino acids 3 to 159; a deletion from amino acids 3 to 194; a deletion from amino acids 3 to 244; a deletion from amino acids 3 to 266; and a deletion from amino acids 3 to 280. Larger deletions which result in smaller proteins may increase solubility of the proteins.

A deletion mutant of the present invention may also contain more than one deletion as long as such deletions are arranged to allow the expression of protein from the nucleic acid sequence encoding the deletion mutant. In one embodiment, any of the above listed deletions at the amino-terminal end of c-jun may be combined with a deletion removing the twenty three carboxy-terminal amino acids of c-jun. One skilled in the art may readily test the deletion mutants of the present invention for their ability to inhibit tumor promoter-induced neoplastic transformation by methods such as the transactivation and soft agar transformation assays described in Examples 5 and 6 for the deletion mutant designated TAM67 containing a deletion of c-jun from amino acids 3 to 122.

Once obtained, nucleic acid sequence encoding the deletion mutants of the present invention may be inserted into a suitable expression vector by methods known to one skilled in the art. By suitable expression vector is meant any vector that is capable of carrying and expressing a complete nucleic acid sequence encoding for a deletion mutant protein of c-jun inhibitory to tumor promoter-induced neoplastic transformation.

Such vectors include any vectors into which a nucleic acid sequence as described above can be inserted, along with any preferred or required operational elements, and which vector can then be subsequently transferred into a host organism and replicated in such organism. Preferred vectors are those whose restriction sites have been well documented and which contain the operational elements preferred or required for transcription of nucleic acid sequence.

The "operational elements" as discussed herein include at least one promoter, at least one operator, at least one leader sequence, at least one determinant, at least one terminator codon, and any other DNA sequences necessary or preferred for appropriate transcription and subsequent translation of the nucleic acid sequence inserted into the vector. In particular, it is contemplated that such constructs will contain at least one origin of replication recognized by the host organism along with at least one selectable marker and at least one promoter sequence capable of initiating transcription of the nucleic acid sequence.

To construct the cloning vector of the present invention, it should additionally be noted that multiple copies of the nucleic acid sequence encoding the deletion mutant(s) and its attendant operational elements may be inserted into each vector. In such an embodiment, the host organism would produce greater amounts per vector of the desired deletion mutant(s) of c-jun. In a similar fashion, multiple different deletion mutants may be expressed from a single vector by inserting into the vector a copy (or copies) of nucleic acid sequence encoding each deletion mutant and its attendant operational elements. In yet another embodiment, a polycistronic vector in which multiple deletion mutants (either identical in sequence or different) may be expressed from a single vector is created by placing expression of each deletion mutant protein under the control of an internal ribosomal entry site (IRES) (Molla A. et al *Nature*, 356:255–257 (1992); PCT Publication Number WO 93/11250). The number of multiple copies of the nucleic acid sequence encoding deletion mutant(s) of c-jun which can be inserted into the vector is limited only by the ability of the resultant vector, due to its size, to be transferred into, and replicated and transcribed in, an appropriate host organism.

Expression vectors suitable for the present method include those vectors capable of producing high efficiency gene transfer in vivo. Such vectors include but are not limited to retroviral, adenoviral and vaccinia viral vectors. Operational elements of such expression vectors are disclosed previously in the present specification and are known to one skilled in the art. A preferred vector is a vector containing the K14 promoter (Vassar, R. and Fuchs, E. (1991) *Genes and Devel.*, 5: 714–727).

An expression vector containing nucleic acid sequence capable of directing host cell synthesis of a deletion mutant of c-jun can be administered in a pure or substantially pure form or as a complex with a substance having affinity for nucleic acid and an internalizing factor bound to the substance having affinity for nucleic acid. (Wu G. et al. J. Biol. Chem 262: 4429–4432 (1987); Wagner E. et al. Proc. Natl. Acad Sci. USA 87: 3655–3659 (1990)). A preferred substance having affinity for nucleic acid is a polycation such as polylysine. Internalizing factors include ligands having specificity for receptors present on the surface of cells susceptible to tumor promoter-induced neoplastic transformation. Such cells include epithelial cells found in tissues such as skin, esophagus, stomach, breasts, intestines, prostate, cervix and the like. Examples of internalizing factors include, but are not limited to, antibodies specific to cell-specific antigens.

Expression vectors containing a nucleic acid sequence encoding deletion mutant protein can be administered intravenously, intramuscularly, intratumorally, topically, subcutaneously, intraperitoneally, orally or as an aerosol. A preferred route of administration is topically or intratumorally. Doses of nucleic acid sequence encoding a deletion mutant effective to elicit prevention of carcinogenesis range from about 100 ng to about 100 μg/kg body weight. A more preferred dose of nucleic acid sequence is about 100 ng to about 10 μg/kg of body weight.

In an alternative embodiment, the deletion mutant of c-jun administered to mammals is a protein. The present invention therefore relates to protein(s) useful as therapeutic agents in the prevention of carcinogenesis and in the treatment of already existing cancers. It is also understood by one skilled in the art that analogs of these proteins are also intended to be encompassed by the present invention.

The term analog as used throughout the specification or claims to describe the proteins of the present invention includes any protein having an amino acid residue sequence substantially identical to a sequence of the deletion mutant (s) of the present invention in which one or more residues have been conservatively substituted with a biologically equivalent residue. By "biologically equivalent" as used throughout the specification and claims, is meant that analogs of the proteins of the present invention are inhibitory to tumor promoter-induced neoplastic transformation. Examples of conservative substitutions include the substitution of one-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that the resulting protein or peptide is biologically equivalent to a deletion mutant of c-jun inhibitory to tumor promoter induced neoplastic transformation.

"Chemical derivative" refers to a deletion mutant protein having one or more residues chemically derivatized by reaction of a functional side group. Examples of such derivatized molecules, include but are not limited to, those molecules in which free amino groups have been derivatized to form amine hydrochlorides, p-toluene sulfonyl groups, carbobenzoxy groups, t-butyloxycarbonyl groups, chloracetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those proteins which contain one or more naturally-occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine; and ornithine may be substituted for lysine.

By tumor promoters as use throughout the specification and claims are meant those compounds able to induce transactivation of gene expression through a c-jun dependent pathway. Such tumor promoters include, but are not limited to, phorbol esters, peptide growth factors, cytokines, various hormones, vinyl plasticizers, environmental pesticides such as dioxin and ultraviolet or ionizing radiation.

The proteins of the present invention may be produced by recombinant methods. The production of these recombinant proteins may be directed by nucleic acid sequences obtained as described earlier in the present specification. In an alternative embodiment, the recombinant protein may be a fusion protein produced by ligating together nucleic acid sequence encoding at least one deletion mutant c-jun with a nucleic acid sequence encoding a protein capable of targeting the recombinant fusion protein to cells susceptible to tumor promoter-induced neoplastic transformation. Proteins capable of targeting the recombinant deletion mutant fusion protein to such cells include, but are not limited to, growth factors and non-neutralizing antibodies specific to cell-specific antigens. The production of such recombinant fusion proteins may be accomplished by techniques known to once skilled in the art.

The nucleic acid sequence capable of directing host organism synthesis of the recombinant protein, whether fused or unfused, may be cloned into a suitable expression vector capable of being transferred into, and replicated in, a host organism. Operational elements of suitable expression vectors are disclosed previously in the present specification and are known to one skilled in the art. Suitable expression vectors can function in prokaryotic or eukaryotic cells. Preferred expression vectors are those that function in eukaryotic cells. Examples of such vectors include, but are not limited to, retroviral vectors, vaccina virus, adeno virus, and adeno-associated virus.

Once a nucleic acid sequence encoding the protein(s) of the present invention is present in a suitable expression vector, the expression vector may then be used for purposes of expressing the protein in a suitable prokaryotic or eukaryotic cell system. Preferred cell systems are eukaryotic cell systems. Such eukaryotic cell systems include, but are not limited to, cell lines such as SF9 insect cells, primate cell lines such as COS cells and human cell lines such as HeLa cells. Preferred eukaryotic cell systems are SF9 insect cells. The expressed protein may be detected by numerous methods known in the art including, but not limited to, metabolic radiolabelling or Western blotting using antibody to appropriate domains of the c-jun protein.

In a further embodiment, the protein expressed by the cells may be obtained as crude lysate or it may be purified by standard protein purification procedures known in the art which may include differential precipitation, molecular sieve chromatography, ion-exchange chromatography, iso-electric focusing, gel electrophoresis, affinity, and immunoaffinity chromatography and the like. In the case of immunoaffinity chromatography, the protein may be purified by passage through a column containing a resin which has bound thereto antibodies specific for c-jun protein.

In an alternative embodiment, the protein(s) may be synthesized by automated instruments sold by a variety of manufacturers or may be custom ordered and prepared.

Once obtained, the protein(s) of the present invention may be administered in a pure or substantially pure form but it is preferable to present it as a pharmaceutical composition, formulation or preparation. Such formulations comprise at least one protein together with one or more pharmaceutically acceptable carriers and optionally other therapeutic ingredients. The formulations may conveniently be presented in unit dosage form and may be prepared by methods well-known in the pharmaceutical art.

All such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous, intramuscular, subcutaneous, or intraperitoneal administration conveniently comprises sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.0M), glycine, and the like, and having a buffered pH compatible with physiological conditions to produce an aqueous solutions, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharide, amino acids, inorganic acids, and organic acids which may be used either on their own or as admixtures. These stabilizers are preferably incorporated in an amount of 0.11–10,000 parts by weight per part by weight of antibody. If two or more stabilizers are used in aqueous solutions at the appropriate concentration and pH. The specific osmotic pressure of such an aqueous solution is generally in the range of 0.1–3.0 osmoses, preferably in the range of 0.80–1.2. The pH of the aqueous solution is adjusted to be within the range of 5.0–9.0, preferably within the range of 6–8. In formulating the protein(s) of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamine acids, polyvinylpyrrolidone, ethylenevinylacetate, methylcellulose, carboxymethyl-cellulose, or protamine sulfate) and the concentration of macromolecules as well as the methods of incorporation in order to control release. Another possible method to control the duration of action by controlled-release preparations is to incorporate the proteins, protein analogs, or their functional derivatives, into particles of a polymeric material such as polyesters, polyamine acids, hydrogels, poly(lactic acid) or ethylene vinylacetate copolymers.

Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly (methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

Methods of administering the protein(s) of the present invention can be conducted by conventional methods. For example, the protein(s) can be used in a suitable diluent such as saline water or in complete or incomplete adjuvants. Doses of protein effective to prevent carcinogenesis range from about 100 ng to about 100 micrograms of protein per kg of body weight. In a more preferred embodiment, doses of protein(s) range from about 100 ng to about 10 μg per kg of body weight. The protein(s) can be administered by any appropriate route such as intravenous, intraperitoneal, intramuscular, subcutaneous, topically, intratumorally, and the like. A preferred route of administration is topically, intramuscularly or subcutaneously at an at-risk site. A protein of the present invention may be administered once or a periodic intervals.

The proteins and expression vectors containing nucleic acid sequences capable of directing host organism synthesis of these proteins may be supplied in the form of a kit, alone, or in the form of a pharmaceutical composition as described above.

The administration of the deletion mutants of the present invention may be for either a prophylactic or therapeutic purpose. When provided prophylactically, the deletion mutant is provided in advance of exposure to a tumor-promoting agent or prior to advanced symptoms of carcinogenesis. The prophylactic administration of the deletion mutant serves to prevent or attenuate any subsequent carcinogenesis in a mammal. When provided prophylactically, the deletion mutant is provided at or after the initiation of carcinogenesis or at the onset of any symptom of carcinogenesis such as the development of benign or pre-neoplastic lesions or a history of cancer. The therapeutic administration of the deletion mutant serves to attenuate the cancer produced by said carcinogenesis.

The present invention therefore also relates to a method for treating cancer in a mammal, said method comprising: administering to a mammal having cancer a pharmaceutical composition comprising at least one deletion mutant of c-jun inhibitory to tumor promoter-induced neoplastic transformation in a therapeutically effective amount. As for the method of prevention disclosed earlier in the specification, the deletion mutant may be administered as a protein as a nucleic acid sequence encoding the protein.

The efficacy of this method of treatment of a mammal having cancer can be monitored by measurement of tumor size by methods known to one skilled in the art, if the cancer manifests itself as a solid tumor or by peripheral blood cell counts if the cancer is blood borne. For example, for skin tumors such as papillomas or carcinomas, one skilled in the art could use calipers to measure tumor size.

In addition to use in methods of treatment and prevention, the deletion mutant(s) of the present invention can be used in a method for determining whether a tumor promoter induces transformation via a c-jun dependent pathway. In one embodiment, the method comprises: (a) transfecting a cell line transformable by treatment with said tumor promoter with nucleic acid sequence encoding a deletion mutant of c-jun inhibitory to tumor promoter-induced neoplastic transformation; (b) treating transfected and untransfected cells with said tumor promoter in an amount effective to stimulate neoplastic transformation of said cells; and (c) measuring transformation of said transfected and untransfected cells by a suitable transformation assay.

Cell lines transformable by tumor promoter treatment include, but are not limited to, JB6 cells, mouse C3H10T1/2 cells and adenovirus-transformed rat embryo fibroblasts. Nucleic acid sequences encoding deletion mutants of c-jun inhibitory to tumor promoter-induced neoplastic transformation have been previously described in the specification. Methods of transiently transfecting cells with nucleic acid sequence are known to once skilled in the art and include such methods as calcium phosphate precipitation, DEAE-Dextran, electropora and lipofection. Alternatively, stable transfectants can be produced by methods known to one skilled in the art including selection by G418 as described in Example 4 of the present specification. Amounts of nucleic acid sequence effective in inhibiting tumor promoter-induced transformation of cells are described in Example 6 and may range from about 1 to about 50 micrograms of DNA per $10^5$ cells. Concentrations of tumor promoter effective to stimulate neoplastic transformation of cells can be readily determined by one skilled in the art using standard dose response curves.

Transformation assays capable of measuring transformation of cells treated with tumor promoter include methods such as soft agarose cloning (Bernstein L. R. et al. (1989) *Science*, 244:566–569) or by monitoring tumorigenicity in nude mice following subcutaneous injection of the tumor promoter-treated cells into the mice. A preferred transformation assay is the soft agar transformation assay described in Example 3 of the present specification. Comparison of the transformation response of transfected and untransfected cells after treatment with the tumor promoter readily allows one skilled in the art to determine whether said tumor promoter induces transformation via a c-jun dependent pathway.

Any articles or patents referenced herein are incorporated by reference. The following examples illustrate various aspects of the invention but are in no way intended to limit the scope thereof.

MATERIALS AND METHODS

The materials and methods used in the following examples were as follows:

Materials

Fetal bovine serum (FBS) was from Whittaker Bioproducts (Walkersville, Md.). TPA was from CCR (Edina, Minn.) and epidermal growth factor (EGF) was from Collaborative Research (Waltham, Mass.). All TPA solutions were dissolved in dimethylsulfoxide (Pierce, Rockford, Ill.) (DMSO) while EGF was dissolved in water. [$^{14}$C]-acetyl coenzyme A and in vivo labeling grade [$^{35}$S]-methionine were from Amersham Corp. (Arlington Heights, Ill.). Lipofectin reagent was from Bethesda Research Laboratories (Gaithersburg, Md.). Fluocinolone acetonide (FA) and retinoic acid (RA) were obtained from Sigma Chemical Co. (St. Louis, Mo.)

Methods

Mouse epidermal JB6 P$^+$ (promotion-sensitive) cells, Cl 41 (deposited with American Type Culture Collection (ATCC), currently awaiting deposit number) and Cl 41.5a, (ATCC Deposit Number CRL 2010) (Colburn, N. H. et al. (1979) *Nature*, 281: 589–591, Colburn, N. H. et al. (1978) In: *Mechanisms of Tumor Promotion and Cocarcinogenesis*, (eds), Slaga, T. J. et al. Raven Press, New York, pp. 257–271, Bernstein, L. R. et al. (1989) *Science*, 244: 566–569) were grown at 36° C. in Eagle's MEM (Whittaker Biosciences) supplemented with 5% heat-inactivated fetal bovine serum and with added 2 mM L-glutamine (Gibco) and 25 pg/ml gentamicin (Quality Biological, Inc.).

Construction of Plasmids

The plasmid constructs used in the following examples were as follows: P750TRCAT is a CAT reporter construct containing 750 bp of the rat stromelysin promoter driving the heterogolous gene chloramphenicol acetyl-transferase (CAT). This construct contains an AP-1 binding sequence at position −70 (Matrisian, L. M. et al. (1991) *Am. J. Medic. Sci.*, 302: 157–162, Kerr, L. D. et al. (1988) *Science*, 242: 1424–1427, McDonnell, S. E. et al. (1990) *Mol. Cell. Biol.* 105 4284–4293). The mTRE-CAT reporter is a site-directed mutant with 2 point mutations in the AP-1 site (Matrisian, L. M. et al. (1991) *Am. J. Medic. Sci.*, 302: 157–162) and the mPEA3-CAT reporter is a site-directed mutant in which point mutations in each of the PEA3 sites at position −208 to −200 and −191 to −199 of the stromelysin promoter were introduced using a protocol provided with the site-directed mutagenesis kit of Amersham Corp. (Arlington Heights, Ill.) and an oligonucleotide having SEQ ID NO.:1 GCAA-GAAGCATTTCTTGG.

The pHIV-CAT reporter plasmid was kindly provided by Dr. David Derse (NCI-Frederick, Cancer Research and Development Center) and its construction is described by Carroll et al. ((1991) *J. Viroloqy* 65:3460–3467). In brief, this reporter construct contains a 196 base pair TaqI-HindIII fragment of the HIV-1 LTR with two NF-κB binding sites linked to the CAT gene.

The pMex MTH-neo TAM67 plasmid is a mammalian expression construct in which TAM67, a truncated transcriptionally inactive form of c-jun (Brown et al (1993)), is under the transcriptional control of the mouse metallothionein-promoter. The pMex MTH-neo vector was constructed by insertion of a 1.8 kb fragment containing the metallothionein I promoter in place of the Moloney sarcoma virus promoter in the eukaryotic expression plasmid pMex-neo (gift of Dr. Mariano Barbacid; Dept. of Molecular Biology, Bristol Meyer Squibb, Princeton, N.J.) The TAM67 sequence was then inserted at the EcoRI site of the vector in the sense direction.

EXAMPLE 1

TPA or EGF-Induced Expression of the Stromelysin-CAT Reporter is Mediated Through the AP-1-Binding Site The gene for the metalloproteinase stromelysin is induced by both TPA and EGF in a cell type-specific manner and its promoter has been shown to contain an AP-1 and several PEA3 (ets binding) elements (Matrisian, L. M. et al. (1991) *Am. J. Medic. Sci.*, 302: 157–162, Kerr, L. D. et al. (1988) *Science*, 242: 1424–1427, Wasylyk, C. et al. (1989) *EMBO. J.*, 8: 3371–3378). In order to assess the role of the AP-1 binding site in the induction of stromelysin-promoter driven transcription, promotion sensitive (P$^+$) clonal genetic variants of the JB6 mouse epidermal cell system were utilized (Colburn, N. H. et al. (1979)) *Nature* (London) 281:589–591)) since AP-1 had been demonstrated to activate gene expression in response to tumor promoters in P$^+$ but not in P$^-$ (promotion-resistant) JB6 cells (Bernstein, L. R. et al. (1989) *Science*, 244:566–569). In brief, JB6 Cl 41 (P$^+$) cells transfected for 4–5 hours using a standard calcium phosphate transfection procedure (Sambrook, J. et al. (1989) "Molecular Cloning, A Laboratory Manual" Cold Spring Harbor Laboratory Press, Cold Spring Harbor, N.Y.) with 10 μg of one of three CAT reporter plasmid DNAs, P750TRCAT, mTRE-CAT or mPEA3-CAT and 10 μg of sheared genomic DNA isolated from Cl 41 cells were then changed to medium containing 2% fetal calf serum and twenty-four to forty-two hours later, were treated with either 0.1% of DMSO, 10 ng/ml of TPA or 10 ng/ml EGF for eight hours prior to preparation of total cell extracts. CAT enzyme activity was assayed using a diffusion-based CAT assay according to the protocol provided by the manufacturers (New England Nuclear, Del.). The results are expressed as the rate of accumulation of [$^{14}$C]-acetylated product relative to solvent controls (DMSO).

The results of this experiment demonstrated that eight hours of TPA or EGF treatment induced about 2-fold higher CAT activity in the P750TRCAT- and mPEA3-CAT-transfected cells than that found in uninduced P750TRCAT- and mPEA3-CAT-transfected cells (FIG. 1). The results also showed that induction of P750TRCAT by either TPA or EGF required the AP-1 binding sequence since mutation of the AP-1 binding site caused loss of inducibility of P750TRCAT. (FIG. 1, compare CAT activity of P750TRCAT transfectants with that of mTRE-CAT transfectants). In contrast, the PEA3 sequence, to which Ets oncoprotein binds (Gunther, C. V. et al. (1990) *Genes Dev.*, 4: 667–669), appeared not to be required for induction by either TPA or EGF as mutations of the PEA3 sites had no effect on inducibility. Finally, the basal activity of these promoters was influenced by both the AP-1 and PEA3 elements since mutation in either of these sites (mTRE-CAT and mPEA3-CAT transfectants respectively) resulted in some decrease in CAT activity in the unstimulated control cultures (DMSO) relative to that observed with P750TRCAT transfectants. Thus, TPA- or EGF-induced activity of the stromelysin CAT reporter was regulated in JB6 cells only by the AP-1 site while basal CAT activity appeared to be regulated by both PEA3 and AP-1 sites.

EXAMPLE 2

TPA-induced AP-1 Activity in P$^+$ Cells Can Be Repressed by Known AP-1 Inhibitors In order to determine whether TPA-induced CAT activity in JB6 P$^+$ cells is capable of being abolished, TPA induced CAT activity was measured in the presence of the known AP-1 inhibitors retinoic acid (RA) and fluocinolone acetonide (FA). In brief, JB6 P$^+$ Cl 41 cells were transfected with 10 $\mu$g of P750TRCAT and 10 $\mu$g of sheared genomic DNA from Cl 41 cells as in Example 1. 24–42 hours after transfection, cells were then exposed for 8 hours to either 0.1% DMSO, 10 $\mu$g/ml TPA alone (TPA), 10$^{-7}$ M fluocinolone acetonide (FA) in the absence of 10 ng/ml TPA (FA7), 10$^{-9}$, 10$^{-8}$ and 10$^{-7}$ M FA in the presence of 10 ng/ml TPA (TFA9, TFA8, TFA7, respectively), 10$^{-5}$ M retinoic acid (RA) in the absence of 10 ng/ml TPA (RA5), or to 10$^{-7}$, 10$^{-6}$ and 10$^{-5}$ M RA in the presence of 10 ng/ml TPA (TRA7, TRA6, TRA5 respectively). Following the above treatments, total cell extracts were prepared and CAT enzyme activity was assayed as in Example 1. As before, the results are expressed as the rate of accumulation of $^{14}$C-acetylated product relative to solvent controls. The results shown in FIG. 2A demonstrate that FA produced dose-dependent inhibition of TPA-induced CAT activity at concentrations of 10$^{-9}$–10$^{-7}$M FA while the results in FIG. 2B demonstrated that RA treatment produced 90–100% inhibition of TPA-induced CAT activity at RA concentrations of 10$^{-7}$–10$^{-5}$M. Taken together, the results presented in FIGS. 2A and 2B demonstrated that TPA-induced AP1 activity can be abolished in JB6 P$^+$ cells.

EXAMPLE 3

Figure 2A:
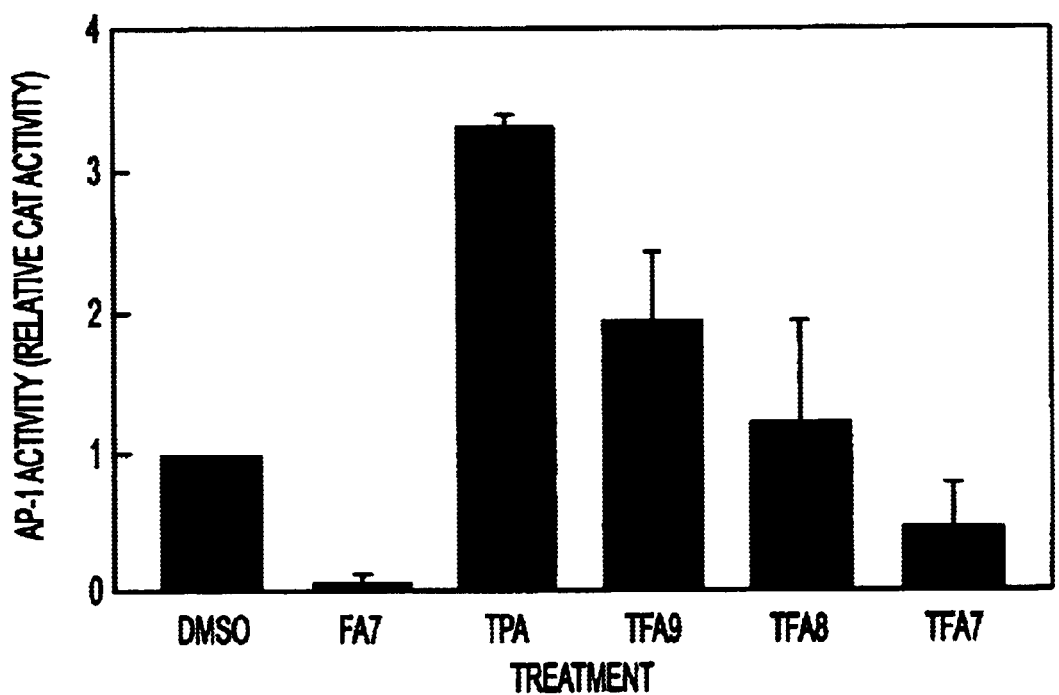
FIGS. 2A and 2B show the results of CAT assays in which aliquots of cell extracts prepared from JB6 P+ Cl 41 cells transfected with 10 µg P750TRCAT and 10 µg sheared genomic DNA isolated from the Cl 41 cells were assayed for CAT activity following treatment for 8 hours with the following compounds.
Figure 2B:
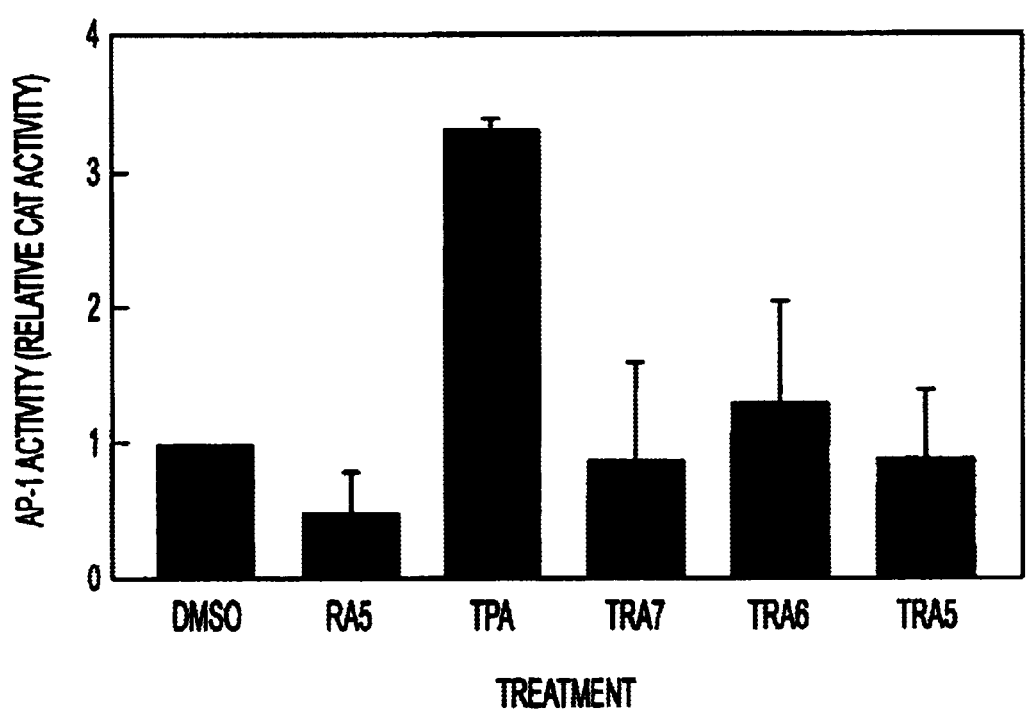
Figure 3A:
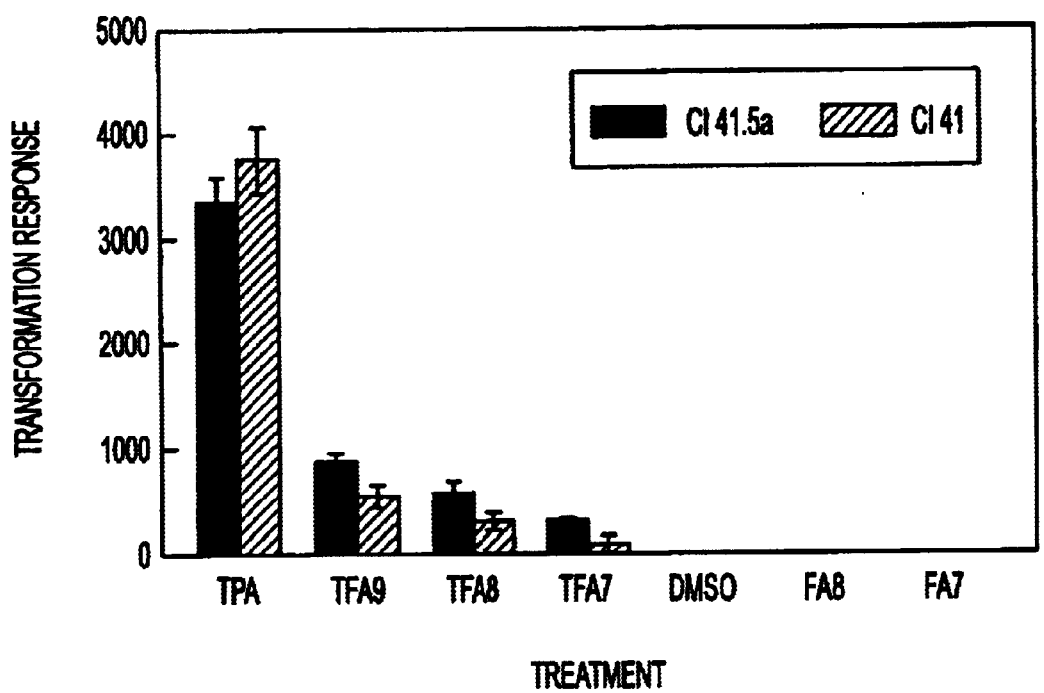
FIGS. 3A and 3B show the results of a soft-agar transformation assay carried out on two JB6 P+ cell lines, Cl 41 (cross-hatched bar) and Cl 41.5a (closed bar), exposed in agar for 14 days to the various compounds indicated on the x-axes of FIGS. 3A and 3B.
Figure 3B:
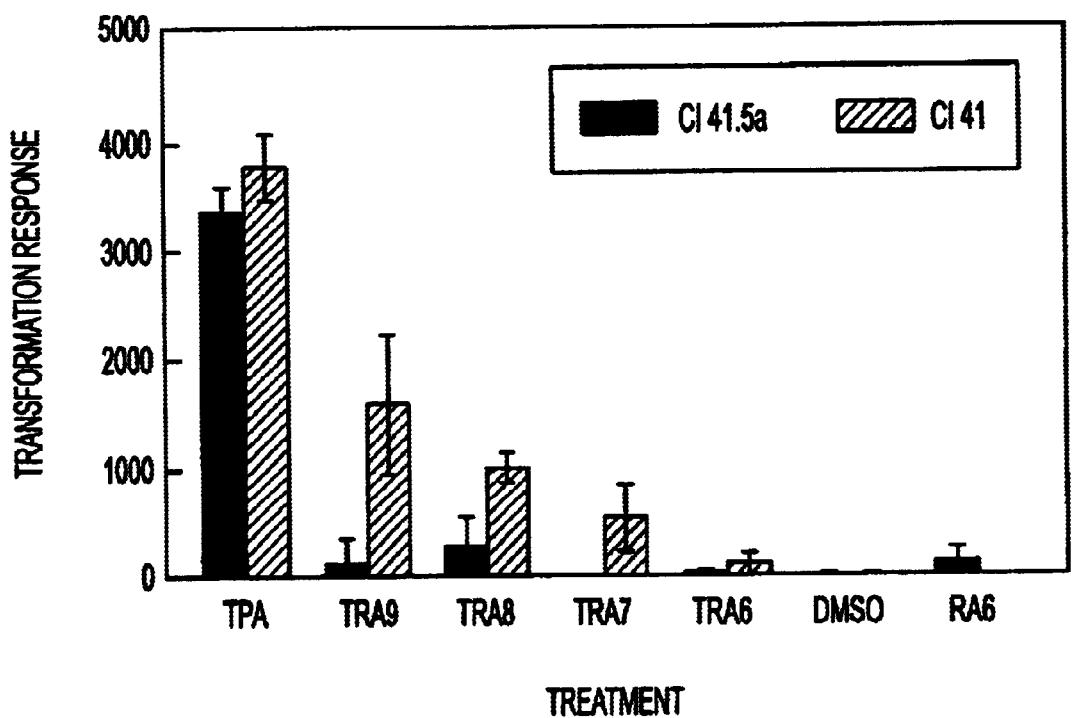

Blockage of TPA Induced Transformation in JB6P$^+$ Cells by Treatment with Retinoic Acid and Fluocinolone Acetonide In order to test whether the same concentration ranges of inhibitors shown in FIGS. 2A and 2B to repress TPA-induced AP-1 activity could also block TPA-induced transformation, a soft agar transformation assay was carried out on JB6 P$^+$ Cl 41 (cross-hatched bar) or JB6 P$^+$ Cl 41.5a (closed bar) cells exposed in 0.33% agar for 14 days to 0.01% DMSO alone, 3 ng/ml TPA alone (TPA), 10$^{-7}$ or 10$^{-8}$ M FA alone (FA7 and FA8, respectively), 10$^{-6}$ M RA alone (RA6) 3 ng/ml TPA in the presence of 10$^{-7}$–10$^{-9}$ M FA (TFA7, TFA8, TFA9) or to 3 ng/ml TPA in 10$^{-6}$–10$^{-9}$ M retinoic acid (TRA6, TRA7, TRA8, TRA9). Treated cells were scored for colonies after 14 days in agar and transformation response was expressed as the number of soft agar colonies/10$^4$ suspended cells. As shown in FIGS. 3A and 3B respectively, FA and RA blocked TPA-induced transformation in a concentration-dependent manner in both P$^\pm$ cell lines. In agreement with an earlier observation by De Benedetti et al. ((1991) *Cancer Res.*, 51:1158–1164), the sensitivity of Cl 41.5a cells to antipromotion by RA appeared to be greater than that observed with the Cl 41 cells. More importantly, the concentration-dependent range of FA effective in blocking TPA-induced transformation appeared identical to that range which was active in blocking TPA-induced CAT activity by FA (10$^{-9}$ M to 10$^{-7}$ M FA, see TFA7, TFA8 and TFA9 in FIG. 2A). By comparison, AP-1-dependent CAT activity was more sensitive to inhibition at 10$^{-7}$ M RA although the concentrations of RA that inhibited TPA-induced CAT activity and transformation did show overlap. Thus, significant inhibition of TPA inducible AP-1 transactivation activity was achieved in P$^+$ cells at doses of RA and FA effective in blocking TPA-induced transformation of JB6 P$^+$ cells.

EXAMPLE 4

Overexpression of the Dominant Negative c-jun Mutant TAM67 in Stably Transfected Cells In order to test whether a dominant negative deletion mutant of c-jun, designated TAM67, (Brown, P. H. et al. (1992) *Oncogene.*, 8:, 877–886, Alani, R. et al. (1991) *Mol. Cell. Biol.*, 11:, 6286–6295) might block AP-1 activity in JB6 P$^+$ cells, pMEX MTH-neo TAM67, a construct containing the TAM67 c-jun mutant inserted into the pMex MTH-neo vector under the transcriptional control of the metallothionein promoter, was utilized. In brief, two $\mu$g of pMEX MTH-neo TAM67 or pMEX MTH-neo vector DNA was transfected using Lipofectin reagent (Bethesda Research Laboratories, Bethesda, Md.) into mouse JB6 P$^+$ Cl 41 cells at 50–70% confluence in 60-mm dishes according to the manufacturer's recommendation (Bethesda Research Laboratories) and the cells were selected in 400 $\mu$g/ml Geneticin (G418, Gibco). Individual clones were then ring-isolated and expanded in the presence of G418 according to standard procedures (Freshney, R. I.: Chapter 13 of "Cloning and Selection of Specific Cell Type in Cultures of Animal Cells". Alan R. Liss, Inc., N.Y., N.Y.) and analyzed for introduced TAM67 expression by Northern blotting using c-jun DNA (Schütte et al. (1989); Ben-Ari et al. (1992) *Mol. Carcinogenesis*, 5: 62–74) as a probe and by immunoprecipitation using rabbit anti-c-jun antibody AB-1 (Oncogene Science, Uniondale, N.Y.). After G418 selection, 8 clonal TAM67 transfectants (M1–M8) and 3 neo-only transfectants (N1–N3) were obtained.

Three TAM67 clonal transfectants (M4, M3, M6) and one neo-only clonal transfectant (N1) were treated for fifteen hours with either 10 ng/ml TPA (T), 10 ng/ml EGF (E), or 0.1% DMSO (D) prior to metabolic labelling for two hours with 0.2 mCi/ml $^{35}$S -methionine (Amersham, Rockford, Ill.) (Sun, Y. et al. (1993) *Mol. Carcinogenesis*, 8: 49–57).

Figure 4:
FIG. 4 shows a sodium dodecyl sulfate polyacrylamide gel electrophoresis (SDS-PAGE) of $^{35}$S-labelled c-jun and TAM67 proteins immunoprecipitated from JB6 P+ Cl 41 cells stably transfected with the pMex MTH-neo TAM67 (TAM67) or the pMex MTH-neo plasmids. The designations M4, M3 and M6 at the top of FIG. 4 indicate the independent clonal TAM67 transfectant cells while the designation N1 indicates independent neo transfectant cells. The stable transfectants were treated for 15 hours with either 10 ng/ml TPA (T), 10 ng/ml EGF (E) or 0.1% DMSO (D) prior to metabolic labeling with $^{35}$S-methionine and immunoprecipitation with a polyclonal rabbit c-jun antibody. The single letter abbreviations used to represent each treatment are shown at the bottom of FIG. 4.

Cellular lysates were then collected and immunoprecipitations using polyclonal rabbit c-jun antibody (AB-1 antibody, Oncogene Science) were carried out overnite at 4° C. (Sun et al. (1993)). These immunoprecipitates were then analyzed by electrophoresis on 12.5% SDS polyacrylamide gels and these gels are shown in FIG. 4. The results clearly demonstrate that the TAM67 transfectants showed expression of the 29 kD TAM67 protein. Moreover, the remaining 5 clonal TAM67 transfectants showed similar expression of the 29 kD TAM67 protein (data not shown). In addition, densitometric analysis of the c-Jun immunoprecipitated protein band (43 kDa) indicated that there was no significant differences in c-Jun protein levels after EGF or TPA treatment in the TAM67 or Neo-only transfectants (FIG. 4 and data not shown). Similarly, with the exception of the M3 clonal transfectant after treatment with EGF, no consistent changes in TAM67 protein levels were observed in the TAM67 transfectants after TPA or EGF treatments.

EXAMPLE 5

Overexpression of the Dominant Neqative C-Jun Deletion Mutant TAM67 in Stably Transfected JB6 Cells Blocks TPA- or EGF-Induced AP-1 Activity In order to determine whether an overexpressed TAM67 protein could repress TPA-induced CAT activity in JB6 $P^+$ cells, eight TAM67 clonal transfectants (M1–M8) and three neo-only clonal transfectants (N1–N3) were transfected with 10 µg of P750TRCAT reporter plasmid using the standard calcium phosphate protocol described in. Example 1. Forty two hours after transfection with P750TRCAT, the cells were exposed to either 0.01% DMSO (closed bar, FIG. 5A), or 10 ng/ml TPA (crossed-hatched bar, FIG. 5A) or, to water (closed bar, FIG. 5B) or 10 ng/ml EGF (cross-hatched bar, FIG. 5B) for eight hours. Total cell extracts were then prepared from the treated cells and assayed for CAT activity as described in Example 1.

Figure 5A:
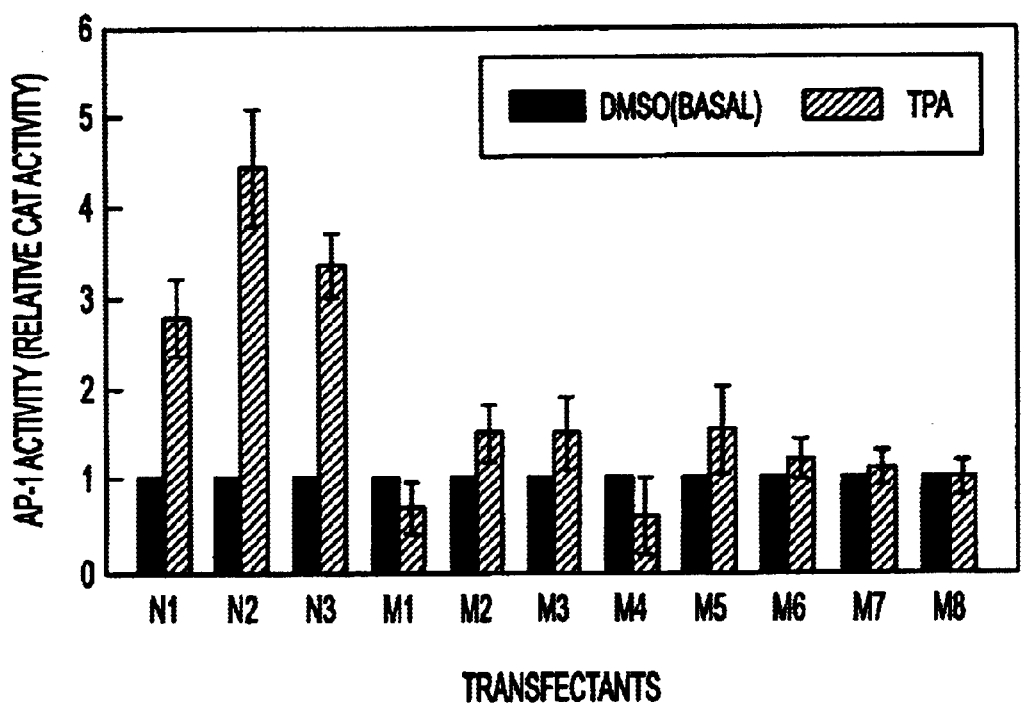
FIGS. 5A and 5B show the results of CAT assays in which aliquots of cell extracts prepared from stably transfected JB6 P+ Cl 41 cells treated as follows were assayed for CAT activity. JB6 Cl 41 cells stably transfected with the pMex MTH-neoTAM67 (TAM67) or the pMex MTH-neo plasmid were subsequently transfected with the P750TRCAT reporter plasmid and then treated for eight hours with either 0.01% DMSO (closed bar, FIG. 5A) or 10 ng/ml TPA (cross-hatched bar, FIG. 5A) or, with water (closed bar, FIG. 5B) or 10 ng/ml EGF (cross-hatched bar, FIG. 5B) as indicated. Results are expressed as the mean±SEM of three independent experiments.
Figure 5B:
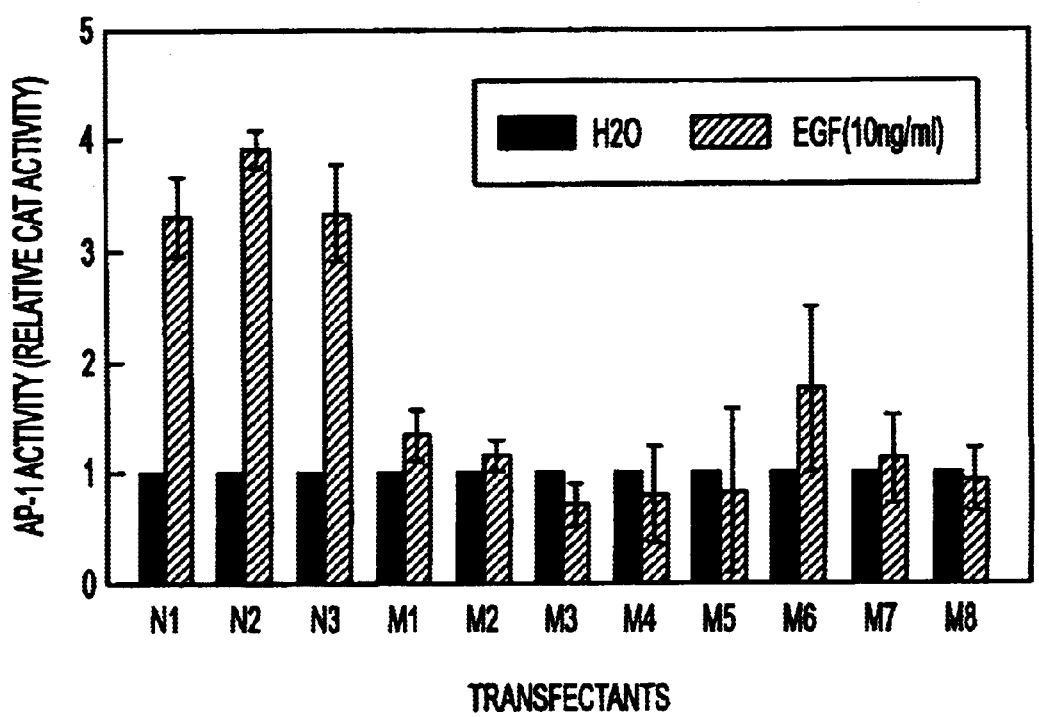

The results shown in FIG. 5A demonstrate that TPA induced 3 to 4.5-fold increases in AP-1 dependent CAT activities in the neo-only transfectants while all 8 of the TAM67 transfectants showed little or no TPA-induced CAT activity. Similar results are observed in FIG. 5B where EGF induced three to four fold increases in AP-1 dependent CAT activities in neo-only transfectants while the eight TAM67 transfectants showed little if any TPA-induced CAT activity. In addition, the basal levels of AP-1 dependent CAT activity were not inhibited by introduced TAM67. Finally, compared to neo-only transfectants, overexpression of TAM67 did not affect monolayer growth rate in medium containing 1%, 3% or 5% fetal calf serum (Data not shown).

To check the possibility that TAM67 might block other TPA or EGF induced transcription factors, a pHIV-CAT reporter construct in which CAT expression is controlled by an HIV-1 promoter sequence containing two NF-κB and no AP-1 sites (Carroll, R. et al. (1991) *J. Virology.*, 65, 3460–3467) was also tested. In brief, HeLa cells were transfected with 10 ug of the PHIV-CAT reporter for 12 hours by calcium phosphate precipitation as described in Example 1. Transfected cells were then treated with 10 ng/ml TPA or 150 units/ml tumor necrosis factor (TNF α) (Boehringer Mannheim, Indianapolis, Ind.) for 3–4 hours prior to harvesting for CAT assays. The results showed that both basal and induced CAT activity following exposure to TPA or TNFA were readily detected in HeLa cells transfected with this construct (Data not shown) suggesting that the induced NF-κB-CAT activity was not affected by cotransfection of TAM67 DNA. Thus, TAM67 specifically blocks induction of c-jun dependent tumor promoter activity in JB6 $P^+$ cells.

EXAMPLE 6

Blockage of TPA- or EGF-induced Transformation in JB6 P+ Cells by TAM67

Figure 6A:
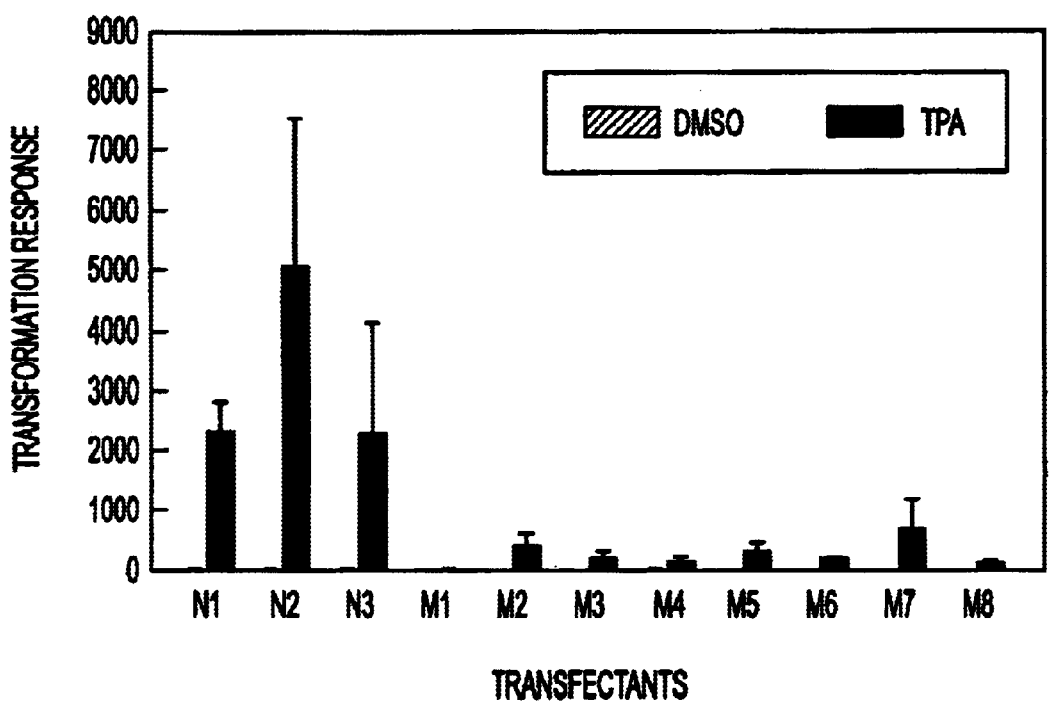
FIGS. 6A and 6B show the results of soft-agar transformation assays carried out on JB6 P+ Cl41 cells stably transfected with the pMex MTH-neoTAM67 plasmid or the pMex MTH-neo plasmid and exposed in agar for 14 days to either 0.01% DMSO (cross-hatched bar, FIG. 6A) or 10 ng/ml TPA (closed bar, FIG. 6A) or, to water (cross-hatched bar, FIG. 6B) or 10 ng/ml EGF (closed bar, FIG. 6B) in 0.33% agar. The designations M1 to M8 refer to independent clonal TAM67 transfectant cells and the designations N1–N3 refer to independent clonal neo transfectant cells. In both FIGS. 6A and 6B, the cells were scored for colonies after 14 days in agar and transformation response was expressed as TPA- or EGF-induced soft agar colonies per $10^4$ suspended cells. Results were expressed as the mean±SEM of three experiments.
Figure 6B:
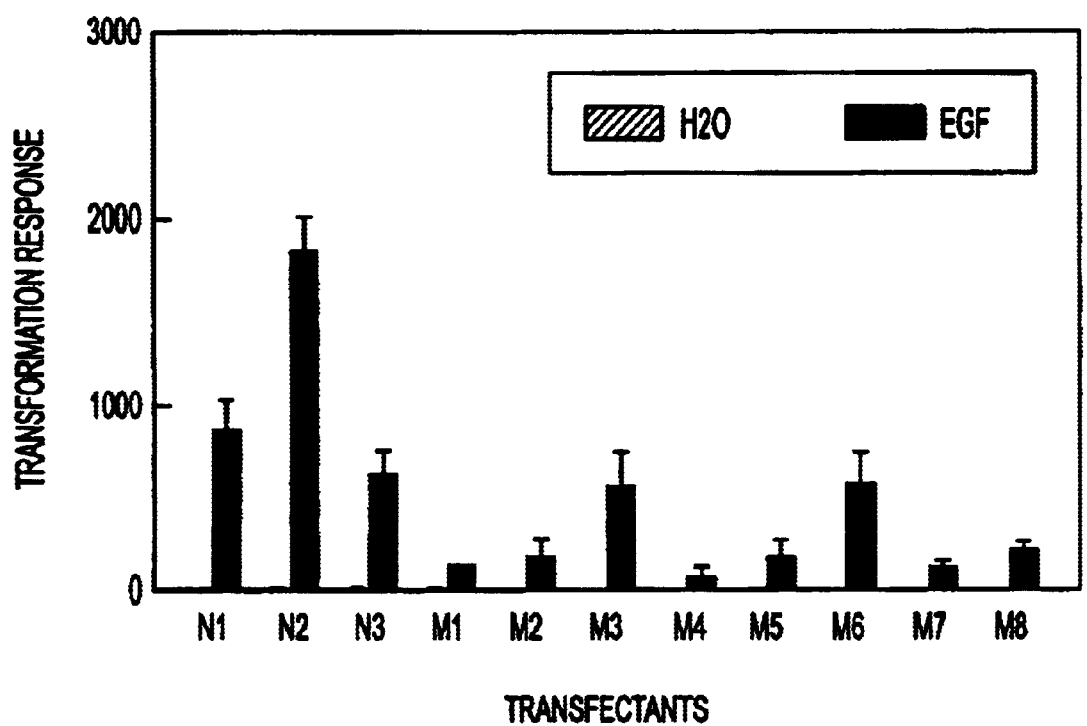

In order to determine whether transfectants stably expressing the TAM67 dominant negative c-jun mutant were able to repress tumor promoter-induced transformation, JB6 Cl 41 cells stably transfected with the pMex MTH-neo TAM67 plasmid or the pMex MTH-neo plasmid were exposed in 0.33% agar for 14 days to either 0.01% DMSO (cross-hatched bars, FIG. 6A) or 10 ng/ml TPA (closed bar, FIG. 6*a*) or, to water (cross-hatched bars, FIG. 6B) or 10 ng/ml EGF (closed bars, FIG. 6B). The treated cells were scored for colonies after 14 days in agar and transformation response was expressed as TPA- or EGF-induced soft agar colonies per $10^4$ suspended cells. The results of the experiments are shown in FIGS. 6A and 6B where the designations M1 to M8 refer to independent clonal TAM67 transfectant cells and the designations N1–N3 refer to independent clonal neo transfectant cells. The results presented in FIG. 6A show that while the three neo-only transfectants exhibited a high frequency of transformation with exposure to TPA, all eight TAM67 c-jun transfectants were blocked for TPA-induced transformation. As shown in FIG. 6B, six of the eight TAM67 transfectants also lost the EGF-induced transformation response while the other two, M3 and M6, showed a transformation response. In summary, knockout of AP-1 response by TAM67 appeared in most cases to produce a loss of transformation response induced by tumor promoters. Finally, it is of interest that transfectants M1 and M4, the highest TAM67 protein expressors, also demonstrated the greatest inhibition of TPA-induced AP-1-dependent CAT activity and transformation.

EXAMPLE 7

Transgenic Mice OverExpressing the TAM67 Dominant Negative C-Jun Deletion Mutant Are Resistant to Tumor-Promoter Induced Carcinogenesis In Vivo by DMBA-TPA In order to direct specific expression of the TAM67 deletion mutant to the squamous epithelia of transgenic mice, the TAM67 cDNA insert is inserted into the K-14 vector (gift of Dr. Elaine Fuchs, Howard Hughes Medical Institute, University of Chicago, Chicago Ill.; Vassar, R. and Fuchs, E. (1991) *Genes and Devel.*, 5: 714–727) under the control of the squamous cell-specific keratin 14 (K14) promoter by blunt end ligation. To check the identity of the resultant construct, K-14 TAM67, PCR is performed using primers from human c-jun (TAM67) and hGH sequences found in the K-14 construct. These primers are shown below as SEQ ID NO. 2 (TAM67) and SEQ ID NO. 3 (hGH) respectively.

SEQ ID NO. 2: CAGGAGCGGATCAAGGCAG and

SEQ ID NO. 3: ACAGGACCCTGAGTGGTT

The K-14 TAM67 insert is then restriction digested out of the plasmid construct according to Vassar et al. (1991) and is purified using a Quiagen kit (QUIAGEN, Chatsworth, Calif.). The K-14 TAM67 insert is then micro injected into male pronuclei from C57BL/6, BALB/C or DBA2 mice at the one cell stage of mouse embryos on day 3.5 of pregnancy (Vassar et al. (1991)). Single blastocysts containing K-14 TAM67 are then implanted into the uterine horn of pseudopregnant mice and the presence of the K-14 TAM67 in mouse founders three weeks after birth is detected by analysis of DNA isolated from the end of the tails of the mice injected with the K-14TAM67. The K-14 TAM67 DNA is detected by PCR using the primers shown in SEQ ID NOS. 2 and 3 or by Southern analysis using c-jun DNA as probe.

The expression of the K-14 TAM67 in tissues from skin, esophagus, stomach, intestines, breasts and other organs of the transgenic mice is evaluated by Northern blots using c-jun DNA (Schutte et al. (1989); Ben-Ari et al. (1992)) as a probe or by immunoprecipitation of TAM67 protein using polyclonal rabbit anti-c-jun antibody (AB-1, Oncogene Science). The side effects of TAM67 expression in the same tissues is analyzed using microscopy and histochemistry to examine organ and tissue morphology and development differentiation markers such as keratin.

The transgenic mice are challenged with an initiating dose of DMBA (7,12-dimethyl-benzanthracene) such as 0.1 umol DMBA/0.2 ml acetone (the initiating dose may vary depending on the strain of mouse utilized) followed one week later by twice weekly challenge with 1–10 μg TPA/0.2 ml acetone. (Naito, M. et al. (1988) *Carcinogenesis*, 9: 639–645). One week after challenge with TPA begins, the transgenic mice are evaluated weekly for protection from carcinogenesis by comparing papilloma and carcinoma formation in the K-14 TAM67 transgenic mice with papilloma and carcinoma formation in transgenic mice containing vector only by visual examination of tumor size and number. Observation of tumor formation over 20–30 weeks in vector-only and K-14 TAM67 transgenic mice demonstrates that the TAM67 transgenic mice do not develop tumors while the vector-only transgenic mice experience tumor formation as evidenced by decreased number and size of papillomas. Thus, the TAM67 deletion mutant of c-jun blocks tumor promoter-induced carcinogenesis in vivo.

EXAMPLE 8

Treatment of Mice Having Epidermal Papillomas and Carcinomas with an Expression Vector Containing the TAM 67 c-Jun Deletion Mutant Either K-14 TAM67 DNA or the corresponding protein/peptide is inspected directly into papillomas and squamous carcinomas growing on the surface of the skin of mice. Both single and repeat injections are-utilized. Measurements of tumor size over time in days using a caliper show that tumor size decreases in mice treated with the K-14 TAM67 nucleic acid sequence or corresponding protein/peptide.

What is claimed is:

1. A method for treating a mammal having a tumor which has AP-1 transcription activity comprising: administering to the mammal a therapeutically effective amount of a DNA construct which encodes a c-jun deletion mutant inhibitory to tumor promoter-induced AP-1 transcription activity.

2. The method of claim 1, wherein the DNA construct encodes a c-jun deletion mutant having a deletion of the transactivation domain.

3. The method of claim 2, wherein the DNA construct comprises TAM67.

4. The method of claim 1, wherein the DNA construct is administered intratumorally.

5. The method of claim 2, wherein the DNA construct is administered intratumorally.

6. The method of claim 3, wherein the DNA construct is administered intratumorally.

7. The method of claim 1, wherein said tumor is a tumor of the skin, esophagus, stomach, breast, intestines, prostate or cervix.

8. The method of claim 2, wherein said tumor is a tumor of the skin, esophagus, stomach, breast, intestines, prostate or cervix.

9. The method of claim 3, wherein said tumor is a tumor of the skin, esophagus, stomach, breast, intestines, prostate or cervix.

10. A method of treating mammalian tumor cells comprising:
    (a) providing a DNA construct encoding a c-jun deletion mutant, said construct being inhibiting to AP-1 transactivation; and
    (b) contacting said mammalian tumor cells with said DNA construct in an amount sufficient to inhibit AP-1 transactivation in said tumor cells.

11. The method of claim 10, wherein said DNA construct encodes a c-jun deletion mutant having a deletion of the transactivation domain.

12. The method of claim 11, wherein the DNA construct comprises TAM67.

* * * * *